(12) United States Patent
Lee et al.

(10) Patent No.: US 8,679,533 B2
(45) Date of Patent: Mar. 25, 2014

(54) PRAMIPEXOLE ONCE-DAILY DOSAGE FORM

(75) Inventors: Ernest J. Lee, Kalamazoo, MI (US);
Gerard M. Bredael, Portage, MI (US);
John R. Baldwin, Kalamazoo, MI (US);
Steven R. Cox, Schoolcraft, MI (US);
Mark J. Heintz, Portage, MI (US)

(73) Assignee: Pharmacia Corporation, Peapack, NJ (US)

( * ) Notice: Subject to any disclaimer, the term of this patent is extended or adjusted under 35 U.S.C. 154(b) by 2238 days.

(21) Appl. No.: 10/626,275

(22) Filed: Jul. 24, 2003

(65) Prior Publication Data

US 2005/0175691 A1 Aug. 11, 2005

Related U.S. Application Data

(60) Provisional application No. 60/398,427, filed on Jul. 25, 2002, provisional application No. 60/398,447, filed on Jul. 25, 2002, provisional application No. 60/479,514, filed on Jun. 18, 2003.

(51) Int. Cl.
*A61K 9/22* (2006.01)
*A61K 9/32* (2006.01)
*A61K 31/428* (2006.01)

(52) U.S. Cl.
USPC ......... 424/468; 424/494; 514/367; 514/772.3

(58) Field of Classification Search
USPC .................................. 424/468, 494; 514/367
See application file for complete search history.

(56) References Cited

U.S. PATENT DOCUMENTS

| | | | |
|---|---|---|---|
| 2,887,440 A | 5/1959 | Greminger et al. | 167/82 |
| 3,065,143 A | 11/1962 | Christenson et al. | |
| 3,074,852 A | 1/1963 | Mayron | |
| 3,458,622 A | 7/1969 | Hill | |
| 3,845,770 A * | 11/1974 | Theeuwes et al. | 424/427 |
| 4,167,558 A | 9/1979 | Sheth et al. | |
| 4,389,393 A | 6/1983 | Schor et al. | |
| 4,666,612 A | 5/1987 | Hoffman et al. | |
| 4,731,374 A | 3/1988 | Griss et al. | 514/367 |
| 4,772,473 A | 9/1988 | Patel et al. | |
| 4,789,549 A | 12/1988 | Khan et al. | |
| 4,859,470 A | 8/1989 | Guittard et al. | |
| 4,968,508 A | 11/1990 | Oren et al. | |
| 5,007,790 A | 4/1991 | Shell | |
| 5,370,879 A | 12/1994 | Masterson et al. | |
| 5,458,887 A | 10/1995 | Chen et al. | 424/464 |
| 5,472,712 A | 12/1995 | Oshlack et al. | 424/480 |
| 5,484,608 A | 1/1996 | Rudnic et al. | |
| 5,656,296 A | 8/1997 | Khan et al. | 424/473 |
| 5,731,338 A | 3/1998 | Acharya | |
| 5,846,971 A | 12/1998 | Sangekar et al. | |
| 5,955,106 A | 9/1999 | Moeckel et al. | |
| 6,056,977 A | 5/2000 | Bhagwat et al. | 424/488 |
| 6,191,153 B1 | 2/2001 | Hammer et al. | |
| 6,197,339 B1 | 3/2001 | Ju | 424/468 |
| 6,277,875 B1 | 8/2001 | Holman | 514/367 |
| 6,316,031 B1 | 11/2001 | Oshlack et al. | |
| 6,417,177 B1 | 7/2002 | Nelson | |
| 6,689,384 B2 | 2/2004 | Tenengauzer et al. | |
| 7,695,734 B2 | 4/2010 | Friedl et al. | |
| 8,545,886 B2 | 10/2013 | Eisenreich et al. | |
| 2001/0041727 A1 | 11/2001 | Marshall et al. | |
| 2001/0042727 A1 | 11/2001 | Riga | |
| 2002/0015735 A1 | 2/2002 | Hedden et al. | 424/488 |
| 2002/0103240 A1 * | 8/2002 | Pospisilik | 514/367 |
| 2002/0182256 A1 | 12/2002 | Oh | |
| 2003/0032661 A1 | 2/2003 | Croenlein | |
| 2003/0049318 A1 | 3/2003 | Davis et al. | |
| 2003/0215498 A1 | 11/2003 | Harland | |
| 2003/0224050 A1 | 12/2003 | Chiao et al. | |
| 2004/0001887 A1 | 1/2004 | Levine et al. | |
| 2004/0068119 A1 * | 4/2004 | Pospisilik | 548/161 |
| 2006/0286168 A1 | 12/2006 | Koike et al. | |
| 2008/0038346 A1 | 2/2008 | Eisenreich et al. | |
| 2008/0069873 A1 | 3/2008 | Pearnchob et al. | |

FOREIGN PATENT DOCUMENTS

| | | |
|---|---|---|
| EP | 0 040 590 A2 | 11/1981 |
| EP | 0425154 | 5/1991 |
| EP | 0 447 168 A2 | 9/1991 |
| EP | 0661045 | 7/1995 |

(Continued)

OTHER PUBLICATIONS

Biglan & Holloway, (2002), *Expert Opinion on Pharmacotherapy*, 3(2), pp. 197-210.
Colosimo & De Michele, (1999), *European Journal of Neurology*, 6(1), pp. 1-21.
Dooley & Markham, (1998), *Drugs & Aging*, 12(6), pp. 495-514.
Hiestand & Smith, (1984), *Powder Technology*, 38, pp. 145-159.
Hiestand & Smith, (1991), *International Journal of Pharmaceutics*, 67, pp. 231-246.
Hubble et al., (1995), *Clinical Neuropharmacology*, 18(4), pp. 338-347.
*Physicians' Desk Reference*, 57 ed. (2003), pp. 2768-2772.
USP $24^{th}$ ed., (2000), pp. 1941-1943.

(Continued)

*Primary Examiner* — John Pak
*Assistant Examiner* — Nathan W Schlientz
(74) *Attorney, Agent, or Firm* — Seth H. Jacobs (57) ABSTRACT

An orally deliverable pharmaceutical composition comprises a therapeutically effective amount of pramipexole or a pharmaceutically acceptable salt thereof and at least one pharmaceutically acceptable excipient, said composition exhibiting at least one of (a) an in vitro release profile wherein on average no more than about 20% of the pramipexole is dissolved within 2 hours after placement of the composition in a standard dissolution test; and (b) an in vivo pramipexole absorption profile following single dose administration to healthy adult humans wherein the time to reach a mean of 20% absorption is greater than about 2 hours and/or the time to reach a mean of 40% absorption is greater than about 4 hours. The composition is useful for oral administration, not more than once daily, to a subject having a condition or disorder for which a dopamine receptor agonist is indicated.

31 Claims, 2 Drawing Sheets

(56) References Cited

FOREIGN PATENT DOCUMENTS

| | | | | |
|---|---|---|---|---|
| EP | 0933079 | 1/1999 | | |
| EP | 0 933 079 | 8/1999 | ............... | A61K 9/20 |
| JP | 10017497 | 1/1998 | | |
| WO | 96/18395 A1 | 6/1996 | | |
| WO | WO 9704752 | 2/1997 | | |
| WO | 97/24109 A1 | 7/1997 | | |
| WO | 9810762 A2 | 3/1998 | | |
| WO | 9901111 A1 | 1/1999 | | |
| WO | WO 9909066 | 2/1999 | | |
| WO | 9916422 A1 | 4/1999 | | |
| WO | 9918932 | 4/1999 | | |
| WO | WO 9916442 | 4/1999 | | |
| WO | 9933448 | 7/1999 | | |
| WO | WO 9945924 | 9/1999 | | |
| WO | 9959563 A2 | 11/1999 | | |
| WO | 00/01369 A1 | 1/2000 | | |
| WO | 00/23055 A1 | 4/2000 | | |
| WO | 00/27370 A1 | 5/2000 | | |
| WO | 0078289 | 12/2000 | | |
| WO | WO 0059477 | 12/2000 | | |
| WO | 01/22944 A1 | 4/2001 | | |
| WO | 01/28516 A2 | 4/2001 | | |
| WO | WO 0122820 | 4/2001 | ............... | A01N 43/78 |
| WO | 01/58447 A1 | 8/2001 | | |
| WO | 0182895 | 11/2001 | | |
| WO | 02/05797 A2 | 1/2002 | | |
| WO | 02/22591 A1 | 3/2002 | | |
| WO | 03/011301 A1 | 2/2003 | | |
| WO | 03/011330 A1 | 2/2003 | | |
| WO | WO 03011255 | 2/2003 | | |
| WO | 03/035042 A1 | 5/2003 | | |
| WO | 03/075887 A1 | 9/2003 | | |
| WO | 03/084504 A2 | 10/2003 | | |
| WO | 03088952 | 10/2003 | | |
| WO | 03103603 | 12/2003 | | |
| WO | 2004/002398 A2 | 1/2004 | | |
| WO | 2004/058228 A1 | 7/2004 | | |
| WO | 2004/058229 A1 | 7/2004 | | |

OTHER PUBLICATIONS

Wright et al. (1997), *Journal of Clinical Pharmacology*, 37, pp. 520-525.
Office Action dated Sep. 4, 2009, U.S. Appl. No. 10/626,166, filed Jul. 23, 2003.
Oct. 5, 2009 Response to Request for Information, U.S. Appl. No. 10/626,166, filed Jul. 23, 2003.
Perez-Marcos et al.; Release of propranolol hydrochloride from matrix tablets containing hydroxypropylmethylcellulose K4M and carbopo 974; International Journal of Pharmaceutics; 1994; vol. 111; pp. 251-259.
Franz et al.; In Vitro Evaluation of a Mixed Polymeric Sustained Release Matrix Using Response Surface Methodology; Journal of Controlled Release; 1987; vol. 5; pp. 159-172.
Bonferoni et al.; Rheological behaviour of hydrophilic polymers and drug release from erodible matrices; Journal of Controlled Release; 1992; vol. 18; pp. 205-212.
Abdallah et al.; Preparation and evaluation of metformin hydrochloride controlled-release tablets; STP Pharma; 1988; vol. 4; pp. 15-20.
Huang et al.; Studies on Drug Release from a Carbomer Tablet Matrix; Drug Development and Industrial Pharmacy; 1995; vol. 21; No. 13; pp. 1487-1501.
Gupta et al.; Hydrogels: from controlled release to pH-responsive drug delivery; Drug Discovery Today; May 2002; vol. 7; No. 10; pp. 569-579.
Li et al.; Effect of HPMC and Carbopol on the release and floating properties of Gastric Floating Drug Delivery System using factorial design; 2003; International Journal of Pharmaceutics; vol. 253; pp. 13-22.
Huber et al.; Utilization of Hydrophilic Gums for the Control of Drug Release from Tablet Formulations I. Disintegration and Dissolution Behavior; Journal of Pharmaceutical Sciences; Sep. 1966; vol. 55; No. 9; pp. 974-976.
Perez-Marcos et al.; Influence of pH on the Release of Propranolol Hydrochloride from Matrices Containing Hydroxypropylmethylcellulose K4M and Carbopol 974; Journal of Pharmaceutical Sciences; Mar. 1996; vol. 85; No. 3: pp. 330-334.
Huber et al.; Utilization of Hydrophilic Gums for the Control of Drug Substance Release form Tablet Formulations II. Influence of Tablet Hardness and Density on Dissolution Behavior; Journal of Pharmaceutical Sciences, 1968; vol. 57; No. 1; pp. 164-166.
BI Sifrol; Dec. 2003, first version, pp. 1-4.
Handbook of Pharm Excip; Cellulose Acetate Phthalate; 2003; pp. 120-122.
Handbook of Pharm Excip; Ethylcellulose, 2003; pp. 237-241.
Handbook of Pharm Excip; Polymethacrylates, 2003; pp. 462-468.
Arnaud et al., Cellulose acetate butyrate microparticles of controlled release of carbamazepine; J. Microencapsulation, 1996, vol. 13, No. 4, pp. 407-417.
Yokoyama et al., Studies on the Metabolic Fate of Pramipexole (SND 919 $CL_2Y$) (II): Absorption and Distribution after Repeated Oral Administration to Rats, Xenobio Metabol and Dispos., 1999, 14(4) pp. 309-314.
Verma, et al., Formulation Aspect in the Development of Osmotically Controlled Oral Drug Delivery Systems, Journal of Controlled Release; 79; 2002; pp. 7-27.
Martindale, Medicines Complete: The Complete Drug Reference; Pramipexole Hydrochloride; 2010.
Physicians' Desk Reference (PDR), $56^{th}$ ed., 2002, Mirapex.
Bodmeier, et al., The Influence of Buffer Species and Strength on Diltiazem HCI Release from Beads Coated with Aqueous Cationic Polymer Dispersions, Eudragit RS, RL 30D, Pharmaceutical Research, vol. 13, No. 1, 1996, pp. 52-56.
Young, et al., Properties of Drug-Containing Spherical Pellets Produced by a Hot-Melt Extrusion and Spheronization Process, J. Microencapsulation, vol. 20, No. 5, Sep.-Oct. 2003, pp. 613-625.
Mani, et al., Solubility of Guaifenesin in the Presence of Common Pharmaceutical Additives, Pharmaceutical Development and Technology, vol. 8, No. 4, 2003, pp. 385-396.
U.S. Appl. No. 60/398,370, filed Jul. 25, 2002.
Abstract in English for Japan JPA320215, 1991.
Abstract in English for Japan JPA7330606, 1995.
Analysis of SIFROL, Actavis, PRM Dissolution Corrected for Sample Withdrawn at Each Time Point, 2013—Submitted by Opponent in Opposition to Counterpart European Patent (EP1536792).
Anasel et al., Introduction of Pharmaceutical Dosage Forms, 5th edition, 1985, pp. 167-170.
Aulton, Pharmaceutics: The Science of Dosage Form Design; First Edition, 1988, Chapter 18.
Bodmeier et al., The Influence of Buffer Species and Strength on Diltiazem HCI Release from Beads Coated with Aqueous Cationic Polymer Dispersions, Eudragit RS, RL 30D, Pharmaceutical Research, 1996, vol. 13, No. 1, pp. 52-56.
Bogentoft et al., Controlled Release From Dosage Forms, Towards Better Safety of Drugs and Pharmaceutical Products, 1980, pp. 229-246.
Bravo et al., Swellable Matrices for the Controlled-release of Diclofenac Sodium: Formulation and In Vitro Studies, Pharmaceutical Development and Technology, vol. 9, No. 1, 2004, pp. 75-83.
British National Formulary, British Medical Association and the Royal Pharmaceutical Society of Great Britain, 2001, p. 242.
Bulletin 2 Product and Regulatory Guide Pharmaceutical Polymers, Noveon, Jan. 2002, pp. 1-3.
Carbomer, 1st Edition, Handbook of Pharmaceutical Excipients, 1986, pp. 41-42.
Dong et al., Effects of Physico-Chemical Properties of Hydroxypropylmethycellulose on Dissolution From Hydrophilic Matrix Tablets, Department of Pharmaceutics, Second Military Medical University, vol. 29, No. 12, 1994, pp. 920-924.
Lieberman et al., Pharmaceutical Dosage Forms: Tablets, vol. 1, 1980, pp. 109-116.
Lu et al., Studies on Sustained Release Hydrophilic Matrix Tablets Containing Hydroxypropylmethycellulose and Carbopol, Department of Pharmaceutics, School of Pharmacy, Fudan University, vol. 36, No. 9, 2001, pp. 603-606.

(56) References Cited

OTHER PUBLICATIONS

Mani et al., Solubility of Guaifenesin in the Presence of Common Pharmaceutical Additives, Pharmaceutical Development and Technology, pp. 385-396, 2003, vol. 8, No. 4.

Note for Guidance on Modified Release Oral and Transdermal Dosage Forms: Section II (Pharmacokinetic and Clinical Evaluation), CPMP, 1999, pp. 1-12.

Ritschel et al., Die Tablette, Hydrophile Matrixtabletten, 2002, p. 140.

Samani et al., The Effect of Polymer Blends on Release Profiles of Diclfenac Sodium from Matices, European Journal of Pharmaceutics and Biopharmaceutics, vol. 55, 2003, pp. 351-355.

Scheife et al.; Impact of Parikinson's Disease and Its Pharmacologic Treatment on Quality of Life and Economic Outcomes: U.S. National Library of Medicine; 2000; XP002314706.

Schmidt et al., Wirk-und Hilfs-stoffe für Rezeptur, Defektur and Großherstellung, 1999, pp. 142-145.

Shannon et al., Efficacy of Pramipexole, A Novel Dopamine Agonist, As Monotherapy in Mild to Moderate Parkinson's Disease, Neurology, 1997, vol. 49, No. 3, pp. 724-728.

Su et al., Adsorption Properties of Heavy Metal Ions From Wastewater with Chitosan-Chelated Bead, Journal of Bejing University of Chemical Technology, vol. 30, No. 2, 2003, pp. 19-22.

Wade et al., Handbook of Pharmaceutical Excipients, Carbomer, 1994, pp. 71-73.

Young et al. Properties of Drug-Containing Spherical Pellets Produced by a Hot-Melt Extrusion and Spheronization Process, Journal of Microencapsulation, 2003, vol. 20, No. 5, pp. 613-625.

* cited by examiner

PRAMIPEXOLE ONCE-DAILY DOSAGE FORM

This application claims priority of U.S. provisional application Ser. No. 60/398,427 filed on Jul. 25, 2002; U.S. provisional application Ser. No. 60/398,447 filed on Jul. 25, 2002; and U.S. provisional application Ser. No. 60/479,514 filed on Jun. 18, 2003.

FIELD OF THE INVENTION

The present invention relates to pharmaceutical formulations of the dopamine receptor agonist pramipexole, and more particularly to sustained-release dosage forms suitable for once-daily administration of pramipexole.

BACKGROUND OF THE INVENTION

Pramipexole (I) is a dopamine $D_2$ receptor agonist useful in treatment of Parkinson's disease. Pramipexole as its dihydrochloride salt is commercially available as Mirapex® tablets of Pharmacia & Upjohn. These are immediate-release tablets in 0.125 mg, 0.25 mg, 0.5 mg, 1.0 mg and 1.5 mg strengths, designed for oral administration of a single tablet three times per day to provide a daily dose of 0.375 to 4.5 mg. See *Physicians' Desk Reference* 57th edition (2003), 2768-2772. Doses herein are expressed in amounts of pramipexole dihydrochloride monohydrate unless otherwise specified; 1.0 mg pramipexole dihydrochloride monohydrate is equivalent to about 0.7 mg pramipexole base.

(I)

A three times daily dosing regimen for immediate-release pramipexole dihydrochloride tablets is well tolerated, but patient compliance would be much improved if a once-daily regimen were possible. In this regard, it will be noted that the primary indication for the drug, Parkinson's disease, is an affliction that becomes more prevalent with advancing age and is often accompanied by decline in memory. A once-daily regimen would be especially useful in enhancing compliance among elderly patients.

In common with other anti-Parkinson's disease drugs, pramipexole has potential to cause undesirable side effects. Side effects of pramipexole have been reported to include orthostatic hypotension, the incidence of which is dose-related. There are also reports of subjects on pramipexole medication experiencing increased somnolence, in particular "sleep attacks". Such attacks involve a subject falling asleep while engaged in activities of daily living, including operation of a motor vehicle, sometimes resulting in accidents. Development of a new once-daily dosage form of pramipexole must take into account the potential to cause such side effects, so that the new dosage form, administered once daily, can be tolerated at least as well as the present immediate-release tablet formulation, administered three times daily.

It is an object of the present invention to provide a once-daily dosage form of pramipexole suitable for oral administration. It is a further object to provide such a dosage form having potential for side effects no greater than a three times daily regimen of pramipexole immediate release tablets. It is a still further object to identify an in vitro release profile that would be characteristic of a well tolerated once-daily dosage form of pramipexole. It is a still further object to identify an in vivo pharmacokinetic (PK) profile that would be consistent with good therapeutic efficacy while not causing an unacceptable incidence or severity of side effects. It is a still further object to provide exemplary dosage forms exhibiting such an in vitro release and/or in vivo PK profile.

Sustained release formulations of many drugs have been described in the literature. For example, U.S. Pat. No. 6,197,339 discloses a sustained-release tablet comprising (R)-5,6-dihydro-5-(methylamino)-4H-imidazo[4,5-ij]-quinolin-2 (1H)-one (Z)-2-butenedioate (1:1) (the dopamine $D_2$ receptor agonist sumanirole maleate) in a matrix comprising hydroxypropylmethylcellulose (HPMC) and starch. The tablet is disclosed to be useful in treatment of Parkinson's disease. Starches disclosed to be suitable therein include pregelatinized starch.

U.S. Pat. No. 5,458,887 discloses a controlled-release tablet comprising an osmotic core that consists of a drug in admixture with a water-swellable component such as HPMC or polyethylene oxide, and a coating that comprises a water-resistant polymer and a minor amount of a water-soluble compound that acts as a pore-former. Upon formation of pores in the coating by dissolution of the water-soluble compound, the water-swellable agent is said to expand the core and provide a drug-rich surface in contact with gastrointestinal fluid.

U.S. Pat. No. 5,656,296 discloses a dual control sustained-release formulation comprising a core that comprises a drug and a low melting point excipient, and a coating layer over the core that comprises a pH-independent water-insoluble polymer and a water-soluble film-forming polymer.

European Patent Application No. EP 0 933 079 discloses a starch said to be suitable for preparing tablets having high hardness yet being capable of rapid disintegration in an aqueous medium. Tensile strength of the finished tablets is calculated from the hardness.

Hubble et al. (1995), *Clinical Neuropharmacology* 18(4), 338-347, described efficacy, safety, tolerability and pharmacokinetics of pramipexole administered three times a day in patients with early Parkinson's disease. A review of pramipexole use in management of early and advanced Parkinson's disease has been published by Dooley & Markham (1998), *Drugs & Aging* 12(6), 495-514. No disclosure is made therein of once-daily administration or sustained-release formulation of pramipexole.

More recently, Biglan & Holloway (2002), *Expert Opinion on Pharmacotherapy* 3(2), 197-210, reviewed pramipexole and its clinical utility in Parkinson's disease and noted that daily dosing with Mirapex® tablets is recommended in patients with impaired renal function, as evidenced by creatine clearance of 15-34 ml/minute. They also indicated that while dopamine receptor agonists generally have been associated with orthostatic hypotension, pramipexole does not appear to cause this complication any more than placebo in randomized controlled trials. It is reported therein, however, that evidence from such trials supports increased incidence of somnolence in patients receiving pramipexole in early Parkinson's disease.

Steady-state PK properties of pramipexole, administered three times a day in the form of pramipexole dihydrochloride tablets, were reported by Wright et al. (1997), *Journal of Clinical Pharmacology* 37, 520-525, who concluded that steady-state PK characteristics were linear up to a daily dose of 4.5 mg, for both men and women.

Patents and publications cited above are incorporated herein by reference.

SUMMARY OF THE INVENTION

There is now provided an orally deliverable pharmaceutical composition comprising a therapeutically effective amount of pramipexole or a pharmaceutically acceptable salt thereof and at least one pharmaceutically acceptable excipient, said composition exhibiting at least one of (a) an in vitro release profile wherein on average no more than about 20% of the pramipexole is dissolved within 2 hours after placement of the composition in a standard dissolution test; and (b) an in vivo pramipexole absorption profile following single dose oral administration to healthy adult humans wherein the time to reach a mean of 20% absorption is greater than about 2 hours and/or the time to reach a mean of 40% absorption is greater than about 4 hours.

There is further provided a method of treatment of a subject having a condition or disorder for which a dopamine receptor agonist is indicated, the method comprising orally administering to the subject, not more than once daily, an orally deliverable pharmaceutical composition comprising a therapeutically effective amount of pramipexole or a pharmaceutically acceptable salt thereof and at least one pharmaceutically acceptable excipient, said composition exhibiting at least one of (a) an in vitro release profile wherein no more than about 20% of the pramipexole is dissolved within 2 hours after placement of the composition in a standard dissolution test; and (b) an in vivo pramipexole absorption profile following single dose oral administration to healthy adult humans wherein the time to reach a mean of 20% absorption is greater than about 2 hours and/or the time to reach a mean of 40% absorption is greater than about 4 hours.

There is still further provided a process for selecting a formulation of pramipexole or a pharmaceutically acceptable salt thereof suitable for sustained-release oral delivery of pramipexole. According to a first embodiment, the process comprises placing a candidate formulation in a dissolution medium under conditions of a standard in vitro dissolution test, wherein if on average no more than about 20% of the pramipexole is dissolved within 2 hours after placement of the candidate formulation in the dissolution medium, the candidate formulation is deemed suitable for selection. According to a second embodiment, the process comprises conducting a standard pharmacokinetic study following single dose oral administration of a candidate formulation to healthy adult humans and deriving an in vivo pramipexole absorption profile from said study, wherein if the time to reach a mean of 20% absorption is greater than about 2 hours and/or the time to reach a mean of 40% absorption is greater than about 4 hours, the candidate formulation is deemed suitable for selection.

The term "orally deliverable" herein means suitable for oral, including peroral and intra-oral (e.g., sublingual or buccal) administration, but compositions of the present invention are adapted primarily for peroral administration, i.e., for swallowing. Where the composition is in the form of a discrete solid article such as a tablet or capsule, it is typically swallowed whole or broken, with the aid of water or other drinkable fluid.

A "therapeutically effective amount" of pramipexole herein is a daily dosage amount that, when administered as part of a regimen, provides therapeutic benefit in treatment of a condition or disorder for which a dopamine receptor agonist is indicated. Suitable amounts per dose are likely to be found in a range from about 0.1 to about 10 mg, preferably about 0.3 to about 5 mg, for example about 0.375, 0.5, 0.75, 1.0, 1.5, 2.0, 3.0 or 4.5 mg, expressed as pramipexole dihydrochloride monohydrate equivalent.

A "standard dissolution test" herein is a test conducted according to *United States Pharmacopeia* 24th edition (2000) (USP 24), pp. 1941-1943, using Apparatus 1 described therein at a spindle rotation speed of 100 rpm and a dissolution medium of 0.05M phosphate buffer, pH 6.8, at 37° C., or other test conditions substantially equivalent thereto.

In vivo "absorption" herein refers to the percentage of pramipexole that enters the bloodstream, as conventionally calculated from data of a standard PK study involving oral administration of a single dose of pramipexole. It will be understood that PK data are subject to the usual variation seen in biological data, thus the absorption percentages specified above are means from a population, typically at least about 8 in number, of individual healthy adults in accordance with standard statistical practice.

A "subject" herein is an animal of any species, preferably mammalian, most preferably human. Conditions and disorders in a subject for which a dopamine receptor agonist is said herein to be "indicated" are not restricted to conditions and disorders for which a dopamine receptor agonist has been expressly approved by a regulatory authority, but also include other conditions and disorders known or believed by a physician to be amenable to treatment with a dopamine receptor agonist. "Treatment" herein embraces prophylactic treatment unless the context requires otherwise.

Compositions of the invention exhibit a number of surprising and unexpected features and benefits.

First, sustained-release dosage forms are typically sought where it is desired to enable longer time intervals between dosing of a drug having a short half-life in plasma, due for example to rapid metabolism, excretion or other routes of depletion. Among drugs used to treat Parkinson's disease, levodopa is a well-known example, having a short elimination half-life ($T_{1/2}$) of about 1.5 hours. See Colosimo & De Michele (1999), *European Journal of Neurology* 6(1), 1-21. By contrast, pramipexole has a $T_{1/2}$ of about 9 to about 14 hours, depending on the particular study, and would not on this ground be expected to require special attention to formulation to enable once-daily dosing.

Second, pramipexole, at least in the form of its dihydrochloride salt, has high solubility in water (about 200 mg/ml at 20-25° C.). Highly water-soluble drugs are typically difficult to formulate in sustained-release form because of the tendency of the drug to rapidly leach out of the dosage form upon exposure to an aqueous medium such as gastrointestinal fluid.

Third, as demonstrated herein, pramipexole dosage forms having very similar in vitro release profiles, as characterized by standard parameters such as time to reach 50% or 80% dissolution, can, as demonstrated herein, have in vivo PK profiles that differ in very meaningful ways. Differences in PK profile between dosage forms having similar 50% and 80% dissolution times in an in vitro test can define the difference between a dosage form that meets the criteria of the present invention and one that does not.

This last finding is especially unexpected in light of a close in vitro/in vivo correlation that is evident for individual dosage forms, as demonstrated herein. It is surprisingly found that data for early time points (up to about 2 hours) and/or initial dissolution rates (up to about 20% dissolution) in the in vitro test described herein are indicative of a PK profile consistent with the present invention. Thus a pramipexole composition exhibiting no more than about 20% dissolution at a 2 hour time point in the in vitro test is strongly indicative of a desirable in vivo PK profile, whereas one exhibiting faster early dissolution, even if 50% and 80% dissolution times are no different, is not so indicative.

These and other features, benefits and advantages of the invention will be apparent from the disclosure that follows.

DETAILED DESCRIPTION OF THE INVENTION

In one embodiment, a pramipexole composition of the invention exhibits at least one of the following:

(a) an in vitro release profile wherein on average no more than about 20% of the pramipexole is dissolved within 2 hours after placement of the composition in a standard dissolution test; and (b) an in vivo pramipexole absorption profile following single dose oral administration to healthy adult humans wherein the time to reach a mean of 20% absorption is greater than about 2 hours and/or the time to reach a mean of 40% absorption is greater than about 4 hours.

Accordingly, in a particular embodiment the composition satisfies at least the in vitro test set forth in (a) above.

In another particular embodiment the composition satisfies at least the in vivo test set forth in (b) above.

To satisfy the in vitro test, on average no more than about 20% of the pramipexole initially included in the composition must dissolve within 2 hours after placement in a dissolution test conducted according to USP 24 using Apparatus 1 at a spindle rotation speed of 100 rpm and a dissolution medium of 0.05M phosphate buffer, pH 6.8, at 37° C., or in a substantially equivalent test. Preferably no more than about 12% of the pramipexole dissolves within 1 hour in such a test. Time to reach 50% dissolution is preferably at least about 4 hours, more preferably at least about 6 hours. Time to reach 80% dissolution is preferably at least about 8 hours, more preferably at least about 12 hours.

To satisfy the in vivo test, a single-dose PK study in healthy adult human subjects must provide data consistent with an absorption profile wherein, at a time point about 2 hours after administration, mean absorption has not yet reached 20%, and/or at a time point about 4 hours after administration, mean absorption has not yet reached 40%. Preferably the time to reach a mean of 40% absorption is at least about 5 hours, more preferably at least about 6 hours.

It is preferred that the composition, when administered once daily, exhibit a bioavailability, as expressed conventionally by $AUC_{0-48}$ or $AUC_{0-\infty}$, that is substantially equivalent to the same daily dose of an immediate-release pramipexole dihydrochloride reference formulation, for example Mirapex® tablets, administered three times a day. In the present context, "substantially equivalent" means that the bioavailability of such a preferred composition is about 0.8 to about 1.25 times that of the reference formulation.

It is preferred that the composition, following single dose administration of 0.375 mg (expressed as pramipexole dihydrochloride monohydrate equivalent), exhibit a maximum plasma concentration ($C_{max}$) of pramipexole that is not greater than about 0.3 ng/ml. Where a higher dose is administered, the preferred upper limit of $C_{max}$ is proportionately greater, it being known that pharmacokinetics of pramipexole are substantially linearly dose-related up to a daily dose of 4.5 mg. Wright et al. (1997), op. cit.

It is preferred that the composition, following single dose administration, exhibit a time to reach maximum plasma concentration ($T_{max}$) of pramipexole that is at least about 6 hours, preferably at least about 8 hours.

It is especially preferred that the composition exhibit a PK profile consistent with steady-state plasma concentrations having a fluctuation ratio that is not substantially greater than that of the reference formulation as defined above. Fluctuation ratio (FR) is defined by the following equation:

$$FR=(C_{max}-C_{min})/C_{avg}$$

where $C_{max}$, $C_{min}$ and $C_{avg}$ are maximum, minimum and average plasma concentrations respectively.

Preferably the PK study used to generate the parameters specified above for a candidate composition is conducted according to a protocol that is generally accepted in the art. Preferably at least 6, more preferably at least 8, most preferably at least 10 subjects are enrolled in the study and receive the candidate composition.

A composition having the in vitro release and/or in vivo PK parameters specified above is advantageous in having reduced potential to cause undesirable side effects that may be related to a combination of high $C_{max}$ and short $T_{max}$, by comparison with other once-daily dosage forms. Preferably the incidence of side effects is no greater than with an immediate-release dosage form such as Mirapex® tablets administered in a three times daily regimen. More preferably, the incidence of side effects is even lower than with such an immediate-release regimen. It is contemplated that these advantages become more pronounced with increase in daily dosage.

A composition of the invention comprises pramipexole or a pharmaceutically acceptable salt thereof, in a therapeutically effective daily dosage amount. It will be understood that mention of pramipexole or another active pharmaceutical agent herein embraces racemates, enantiomers, polymorphs, hydrates and solvates thereof. Pramipexole is used preferably in the form of its S-enantiomer, (S)-2-amino-4,5,6,7-tetrahydro-6-(propylamino)-benzothiazole.

It is preferred to use a salt of pramipexole, especially a salt exhibiting moderate to high solubility in water. Illustrative salts include those prepared using the following acids: hydrochloric, hydrobromic, hydroiodic, phosphoric, sulfuric, methanesulfonic acid, ethanesulfonic, 2-hydroxyethanesulfonic, benzenesulfonic, p-hydroxybenzoic, toluenesulfonic, formic, acetic, propionic, benzoic, anthranilic, tartaric, maleic, malic, citric, isocitric, succinic, ascorbic, lactic, glycolic, gluconic, glucuronic, pyruvic, oxaloacetic, fumaric, aspartic, glutamic, stearic, salicylic, phenylacetic, mandelic, pamoic, pantothenic, sulfanilic, cyclohexylaminosulfonic, algenic, β-hydroxybutyric, galactaric and galacturonic acids.

A preferred salt of pramipexole is the dihydrochloride salt, most preferably in the form of the monohydrate.

Pramipexole and salts thereof, including the dihydrochloride salt, useful herein can be prepared by processes known per se, including processes disclosed in patents and other literature pertaining to pramipexole.

The composition can take any form suitable for oral administration, but is typically formulated as a discrete solid dosage unit such as a tablet or capsule, wherein the pramipexole or salt thereof is present as solid particles, and is formulated together with one or more pharmaceutically acceptable excipients. The excipients are selected in part to provide a release profile and/or PK profile consistent with those defined above.

The amount of pramipexole present in a composition of the invention is sufficient to provide a daily dose in one to a small plurality, for example one to about 4, of dosage units to be administered at one time. Preferably the full daily dose is delivered in a single dosage unit. An amount of about 0.1 to about 10 mg per dosage unit, or about 0.05% to about 5% by weight of the composition, will generally be suitable. Preferably an amount of about 0.2 to about 6 mg, more preferably an amount of about 0.3 to about 5 mg, pramipexole per dosage unit is present. Specific amounts per tablet contemplated herein include 0.375, 0.5, 0.75, 1.0, 1.5, 3.0 and 4.5 mg pramipexole dihydrochloride monohydrate.

The particular formulation selected for the pramipexole is not critical so long as it achieves a release and/or PK profile as defined herein. Such a profile can be achieved using one or more release-modifying means. Illustratively, release-modifying means suitable for use in a composition of the invention include a polymer matrix wherein the pramipexole is dispersed; a release-controlling layer or coating surrounding the whole dosage unit or pramipexole-containing particles, granules, beads or zones within the dosage unit; and an osmotic pump.

In one embodiment, the composition takes the form of a tablet comprising pramipexole or a salt thereof, dispersed in a matrix comprising a hydrophilic polymer and starch. Preferably the starch has a tensile strength of at least about 0.15 kN cm$^{-2}$ at a solid fraction representative of the tablet, for example about 0.75 to about 0.85, illustratively 0.8.

Hydrophilic polymers useful according to the present embodiment are pharmaceutically acceptable polymeric materials having a sufficient number and distribution of hydrophilic substituents such as hydroxy and carboxy groups to impart hydrophilic properties to the polymer as a whole. Suitable hydrophilic polymers include, without limitation, methylcellulose, HPMC (hypromellose), carmellose sodium (sodium carboxymethylcellulose) and carbomer (polyacrylic acid). More than one such polymer can optionally be used.

HPMC is a preferred hydrophilic polymer. Various types and grades of HPMC are available. In one embodiment HPMC type 2208, preferably meeting specifications set forth in a standard pharmacopeia such as USP 24, is used. HPMC type 2208 contains 19-24% by weight methoxy and 4-12% by weight hydroxypropoxy substituents. Especially suitable HPMCs have nominal viscosity ranging from about 100 to about 10,000 mPa s; illustratively a suitable HPMC type 2208 is one having a nominal viscosity of about 4,000, with a measured viscosity of about 3,000 to about 5,600 mPa s. Such an HPMC is available, for example, as Methocel® K4 MP from Dow Chemical Co., and substantially equivalent products are available from other manufacturers.

The amount of hydrophilic polymer in the composition depends on the particular polymer selected, on the active pharmaceutical agent and on the desired sustained release profile. Typically, however, the hydrophilic polymer is included in an amount of about 20% to about 70%, preferably about 30% to about 60% and more preferably about 35% to about 50%, by weight of the composition. In the illustrative case of HPMC type 2208, a suitable amount will generally be found in the range from about 30% to about 60%, preferably about 35% to about 50%, for example about 40%, by weight of the composition.

It is believed, without being bound by theory, that the hydrophilic polymer functions to provide extended or sustained release of the pramipexole, for example by gradual dissolution or erosion of the polymer in the gastrointestinal tract.

Starches useful herein include starches from any suitable botanical source, for example corn, wheat, rice, tapioca, potato, etc. Preferred starches have a relatively high ratio of amylose to amylopectin, containing for example at least about 20%, more preferably at least about 25%, amylose. Especially preferred is pregelatinized starch, which is a type of modified starch that has been processed to render the starch more flowable and directly compressible. Partially or wholly pregelatinized starches can be used.

It is believed, without being bound by theory, that the primary function of the starch in a composition of the present embodiment is as a binding agent. A starch meeting the preferred tensile strength criterion defined herein is sometimes referred to herein as a "super binder".

The amount of starch in a composition of the present embodiment is typically higher than is conventionally present as a binder in tablet formulations. Suitable amounts will generally be found in the range of about 25% to about 75% by weight. Preferably the amount of starch is about 40% to about 70%, more preferably about 45% to about 65%, for example about 50%, by weight of the composition.

Tensile strength of a starch sample can be measured by any suitable test. Illustrative test procedures are described by Hiestand & Smith (1984), *Powder Technology* 38, 145-159, and by Hiestand & Smith (1991), *International Journal of Pharmaceutics* 67, 231-246, these articles being incorporated herein by reference.

An example of a tensile strength test that can be used (herein referred to as a "triaxial tensile strength test") requires preparation of a series of compacts of the starch sample, followed by determination of tensile strength of the compacts using a computerized multifunction tablet tester (MTT). The compacts are prepared with various degrees of compression force to provide compacts having a range of solid fraction. As a sustained release tablet formulation typically has a solid fraction of about 0.8, it is useful to prepare compacts approximating such a solid fraction.

Absolute density of the starch sample can be determined using a helium-air pycnometer.

A computer-controlled triaxial tablet press is used to prepare the compacts. Voltage output from the punch and die load cells of the tablet press are first zeroed. The punch and die are lubricated with magnesium stearate powder and the die assembly is placed in the press. Compression and decompression parameters are selected on the computer. The desired amount of starch to be compacted is weighed and poured into the die cavity. The resulting powder bed is leveled with a spatula. The punch is inserted into the die and the computer-controlled compression/decompression cycle is started.

Just prior to the end of the compression phase, thickness of the compact as measured by LVDT is recorded. At the end of the compression phase, the final compression force as measured by voltage of the punch load cell is recorded.

At the end of the decompression phase, the punch and die rams are retracted. The compact is removed from the die and inspected for defects, such as cracking or sticking. Cracking can be reduced by increasing decompression time. If the compact is free of defects, its length, width, thickness and weight are measured to enable calculation of apparent density. Solid fraction is calculated by dividing absolute density by apparent density.

In preparation of the MTT for tensile strength determination, a suitable software program is run. The platen is screwed to the load cell of the MTT and the tensile strength assembly is slid into the MTT opposite the platen. The load cell signal is monitored via the computer and the zero offset on the signal conditioner is adjusted to provide a positive baseline voltage as close as possible to zero. A forward velocity is selected that will generate a time constant of approximately 15 seconds (usually the velocity selected will be about 0.8 to about 1.2 mm s$^{-1}$).

The compact to be tested is placed in the holder of the tensile strength assembly. The motor is initiated via the computer, driving the platen toward the compact until the surface of the compact is detected, and stopping the platen a few millimeters from the compact. The oscilloscope is triggered, to record the force applied to the compact, and the motor is restarted. The platen is driven into the compact until a crack is detected, either by sight or by sound, and the motor is immediately reversed.

Peak force is recorded from the oscilloscope trace. Tensile strength is calculated from the peak force using appropriate computer software.

From several runs using compacts at a range of solid fractions around 0.8, data are plotted and tensile strength at a solid fraction of 0.8 is estimated. If the tensile strength at a solid fraction of 0.8 is about 0.15 kN cm$^{-2}$ or greater, the starch sample is deemed to be suitable for use in preparing a composition according to the present embodiment of the invention.

It has now surprisingly been discovered that a much simpler test, one that is more amenable to implementation in a manufacturing setting, can be used to estimate tensile strength of a starch sample, in particular to determine whether the starch sample has a tensile strength of at least about 0.15 kN cm$^{-2}$ at a solid fraction representative of a desired sustained-release tablet.

According to this test, compacts of the starch sample are prepared on a standard automated tablet press under a range of compression forces. For example, a Carver press (e.g., Model 3888.1DT0000) fitted with flat-faced tooling of suitable diameter (e.g., $^{10}/_{32}$ inch or about 0.7 cm for a 300 mg compact), operated at compression forces of about 4 to about 16 kN (about 900 to about 3600 lbf) for a dwell time of at least about 4 seconds has been found to give satisfactory results. Illustratively, such compacts can be prepared at 1000, 1500, 2000 and 3000 lbf (4.45, 6.67, 8.90 and 13.34 kN). Preferably a dwell time of at least about 10 seconds, more preferably at least about 30 seconds, still more preferably at least about 60 seconds, is used. Illustratively, a dwell time of 90 seconds has been found to give satisfactory results. Weight, diameter and thickness of each compact are measured accurately (alternatively, diameter can be assumed to equal that of the tooling) to enable calculation of apparent density and hence solid fraction, absolute density having been measured as described above, for example by helium-air pycnometry.

Hardness of each compact thus prepared is then determined by any suitable tablet hardness test, for example using a Key HT 500 hardness tester. Hardness is a measure of the force required to cause crushing of the compact, and is typically expressed in units such as kiloponds (kp) or Strong-Cobb units (SCU). A hardness of about 10.2 kp or about 14.4 SCU corresponds to a force of 0.1 kN.

For present purposes it is considered that crushing strength of the compact is equivalent to tensile strength. Thus tensile strength ($\sigma_T$, in kN cm$^{-2}$) can be calculated from the equation $$\sigma_T = 2F/\pi DH$$

where F is the force required to cause crushing (in kN), D is diameter of the compact (in cm) and H is thickness of the compact (in cm). For example, a compact of diameter 0.7 cm and thickness 0.4 cm having a hardness of 20 SCU (equivalent to a force of 0.139 kN) has a calculated tensile strength of 0.316 kN cm$^{-2}$.

The relationship between tensile strength and solid fraction is next established for the starch sample. This can be done by plotting data for tensile strength and solid fraction on a graph (solid fraction tends to increase with increasing compression force during preparation of the compact) or by performing a regression analysis. From that relationship, tensile strength at a standardized value of solid fraction can be estimated. The standardized value selected is one that is representative of the solid fraction of a desired sustained-release tablet, e.g., 0.8.

Where the material of the compact is pregelatinized starch, it has been found that tensile strength as determined in a simple test as described immediately above is surprisingly close to a "true" tensile strength measurement as determined by the triaxial tensile strength test method previously described, which in turn is essentially similar to methods known in the art such as that disclosed by Hiestand & Smith (1984), op. cit.

It has also been found that a longer dwell time (e.g., 90 seconds) in the test method of the present invention gives a better correlation with triaxial tensile strength than a very short dwell time (e.g., 4 seconds). See Example 1 below and FIGS. 1 and 2.

An especially preferred starch has a tensile strength of at least about 0.175 kN cm$^{-2}$, even more preferably at least about 0.2 kN cm$^{-2}$, at a solid fraction representative of a desired sustained-release tablet.

Even among commercially available pregelatinized starches, the preferred type of starch for use in a composition of the present embodiment, considerable variation exists in tensile strength. Pregelatinized starches not meeting the tensile strength criterion established herein are not readily identified without testing, for example by a method as disclosed above. Such pregelatinized starches are generally unsuitable for commercial-scale manufacture of a sustained-release matrix tablet formulation of pramipexole, because of a problem as set forth immediately below.

An uncoated tablet, or a tablet core prior to coating, comprising starch and a hydrophilic polymer acting as a matrix for a water-soluble drug or prodrug requires to have a certain minimum hardness in order to be able to resist breakage and/or attrition due to mechanical stresses imposed during a high-speed tableting operation (including all steps up to and including filling of the tablets into containers). The minimum acceptable hardness will depend on a number of factors, including the severity of the mechanical stresses, but is typically at least about 20 SCU, preferably at least about 22 SCU, more preferably at least about 24 SCU (about 17 kp).

Figure 3:
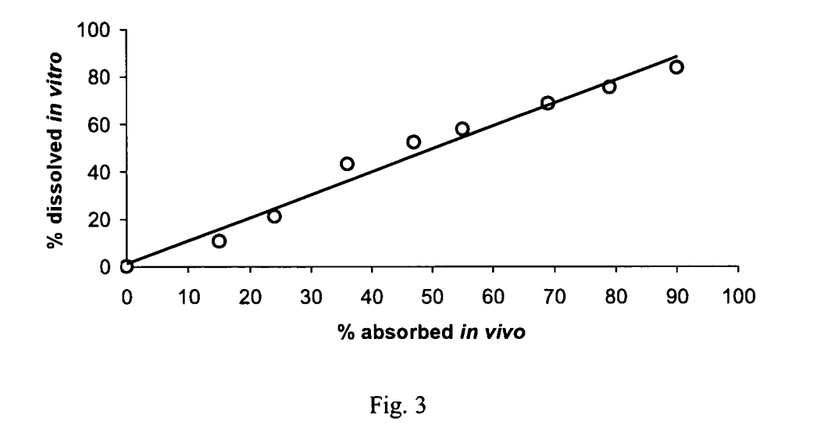
FIG. 3 shows in vitro/in vivo correlation for the pramipexole dihydrochloride tablets of Example 1.

Hardness can be increased by increasing the compression force applied by the tablet press, but only up to a certain level. At least in the case of tablets as described herein, above a certain compression force, further increases in compression force give little or no further increase in tablet hardness. There is, in other words, a maximum hardness achievable by compression of a particular starch/hydrophilic polymer/active agent composition. A starch providing a maximum hardness inadequate to withstand the mechanical stresses of a high-speed tableting operation is unsuitable for the present purpose. As shown in FIG. 3, certain pregelatinized starches have been found to provide a maximum hardness of 20 SCU or less; these are now identified as starches having low tensile strength (0.1 kN cm$^{-2}$ or less according to the test method of the invention utilizing a dwell time of 90 seconds).

Even if a maximum hardness of at least about 20 SCU is achievable, with a starch of low tensile strength it may be achievable only by use of extremely high compression forces. A requirement for such forces reduces speed and efficiency and increases cost of a tableting operation and is undesirable for these reasons.

Where tablets are to be subjected to an additional process step after compression, in particular a coating step, exposure to mechanical stresses is greatly increased. According to a preferred embodiment, therefore, the sustained-release tablet of the invention further comprises a coating.

Particularly for a highly water-soluble salt such as pramipexole dihydrochloride, a hydrophilic polymer matrix is often inadequate to provide sustained release of sufficiently long duration to permit once daily administration. It is believed that such a salt is readily leached out of the hydrophilic matrix when contacted by an aqueous medium such as gastrointestinal fluid. It is therefore desirable to further slow the process of drug release by providing a release-controlling coating around the tablet. Such a coating typically comprises a hydrophobic or water-insoluble polymer component such as ethylcellulose together with a hydrophilic or water-soluble pore-forming component such as HPMC.

Where a starch is used having a tensile strength of at least about 0.15 kN cm$^{-2}$, preferably at least about 0.175 kN cm$^{-2}$, more preferably at least about 0.2 kN cm$^{-2}$, at a solid fraction representative of the tablet (e.g., about 0.75 to about 0.85), the composition is found to be especially suited to a high-speed tableting operation that includes a step of coating the tablet with a release-controlling layer.

Alternatives to ethylcellulose and HPMC as components of a release coating layer include other cellulosic polymers (e.g., methylcellulose, hydroxypropylcellulose, hydroxyethylcellulose, carboxymethylcellulose sodium, cellulose esters such as cellulose acetate, etc.), polyvinyl acetate, polyvinyl pyrrolidone, polymers and copolymers of acrylic acid and methacrylic acid and esters thereof, polyethylene glycol, carrageenan and other gums, and the like.

A release-controlling layer, if present, typically constitutes about 1% to about 15%, preferably about 2.5% to about 10%, by weight of the tablet as a whole. The hydrophobic or water-insoluble component, preferably comprising ethylcellulose, typically constitutes about 1% to about 10%, preferably about 2% to about 7%, by weight of the tablet as a whole. The pore-forming component, preferably comprising HPMC, is typically present in an amount of about 5% to about 50%, preferably about 10% to about 40%, by weight of the water-insoluble or hydrophobic component.

The coating, if present, can optionally contain additional pharmaceutically acceptable excipients such as plasticizers, dyes, etc.

Illustratively, a release-controlling layer in an amount of about 2.5% to about 5% by weight of the tablet core (i.e., the tablet weight excluding the coating) comprises an ethylcellulose-based material (e.g., Surelease® of Colorcon) and an HPMC-based pore-forming material (e.g., Opadry® of Colorcon) in a weight ratio of about 3:1 to about 4:1.

A release-controlling layer or coating should be applied at as uniform a thickness as possible to provide optimum control of release rate of the pramipexole.

Alternatively or in addition, the sustained-release tablet of the invention comprises a nonfunctional coating. A nonfunctional coating can comprise a polymer component, for example HPMC, optionally with other ingredients, for example one or more plasticizers, colorants, etc. The term "nonfunctional" in the present context means having substantially no effect on release properties of the tablet, and should not be read to imply that the coating serves no useful purpose. For example, such a coating can impart a distinctive appearance to the tablet, provide protection against attrition during packaging and transportation, improve ease of swallowing, and/or have other benefits. A nonfunctional coating should be applied in an amount sufficient to provide complete coverage of the tablet. Typically an amount of about 1% to about 10%, more typically an amount of about 2.5% to about 5%, by weight of the tablet as a whole, will be found suitable.

Uncoated tablets and cores of coated tablets of the present embodiment can optionally contain one or more pharmaceutically acceptable excipients in addition to the starch and hydrophilic polymer components described above. Such excipients include without limitation glidants and lubricants. Other conventional excipients known in the art can also be included.

A glidant can be used to improve powder flow properties prior to and during tableting and to reduce caking. Suitable glidants include colloidal silicon dioxide, magnesium trisilicate, powdered cellulose, starch, talc, tribasic calcium phosphate and the like. In one embodiment, colloidal silicon dioxide is included as a glidant in an amount up to about 2%, preferably about 0.2% to about 0.6%, by weight of the tablet.

A lubricant can be used to enhance release of a tablet from apparatus on which it is formed, for example by preventing adherence to the face of an upper punch ("picking") or lower punch ("sticking"). Suitable lubricants include magnesium stearate, calcium stearate, canola oil, glyceryl palmitostearate, hydrogenated vegetable oil, magnesium oxide, mineral oil, poloxamer, polyethylene glycol, polyvinyl alcohol, sodium benzoate, sodium lauryl sulfate, sodium stearyl fumarate, stearic acid, talc, hydrogenated vegetable oil, zinc stearate and the like. In one embodiment, magnesium stearate is included as a lubricant in an amount of about 0.1% to about 1.5%, preferably about 0.3% to about 1%, by weight of the tablet.

Tablets can be of any suitable size and shape, for example round, oval, polygonal or pillow-shaped, and optionally bear nonfunctional surface markings. Especially in the case of coated tablets they are preferably designed to be swallowed whole and are therefore typically not provided with a breaking score. Dosage unit compositions of the invention can be packaged in a container, accompanied by a package insert providing pertinent information such as, for example, dosage and administration information, contraindications, precautions, drug interactions and adverse reactions.

There is also provided a method of treatment of a subject having a condition or disorder for which a dopamine $D_2$ receptor agonist is indicated, the method comprising orally administering to the subject, not more than once daily, an orally deliverable pharmaceutical composition comprising a therapeutically effective amount of pramipexole or a pharmaceutically acceptable salt thereof and at least one pharmaceutically acceptable excipient, said composition exhibiting at least one of:

(a) an in vitro release profile wherein no more than about 20% of the pramipexole is dissolved within 2 hours after placement of the composition in a standard dissolution test as defined herein; and (b) an in vivo pramipexole absorption profile following single dose administration to healthy adult humans wherein the time to reach a mean of 20% absorption is greater than about 2 hours and/or the time to reach a mean of 40% absorption is greater than about 4 hours.

The method is particularly useful where the condition or disorder is Parkinson's disease or a complication associated therewith.

Suitable daily dosage amounts of pramipexole include 0.375, 0.5, 0.75, 1.0, 1.5, 3.0 and 4.5 mg, expressed as pramipexole dihydrochloride monohydrate.

EXAMPLES

Example 1

Pramipexole dihydrochloride sustained-release tablets were prepared having the compositions shown in Table 1.

TABLE 1

Composition of pramipexole dihydrochloride tablets of Example 1

| Ingredient | Amount (mg) | | | | | | | |
|---|---|---|---|---|---|---|---|---|
| pramipexole dihydrochloride monohydrate | 0.375 | 0.75 | 1.5 | 3.0 | 4.5 | 0.375 | 0.375 | 4.5 |
| HPMC type 2208, 4000 mPa s | 140.0 | 140.0 | 140.0 | 140.0 | 140.0 | 70.0 | 157.5 | 157.5 |
| pregelatinized starch | 206.5 | 206.1 | 205.4 | 203.9 | 202.4 | 101.5 | 189.0 | 184.9 |
| colloidal silicon dioxide | 1.4 | 1.4 | 1.4 | 1.4 | 1.4 | 1.4 | 1.4 | 1.4 |
| magnesium stearate | 1.75 | 1.75 | 1.75 | 1.75 | 1.75 | 1.75 | 1.75 | 1.75 |
| total | 350 | 350 | 350 | 350 | 350 | 175 | 350 | 350 |

All ingredients except the lubricant (magnesium stearate) were screened to remove lumps and were blended thoroughly in a low-shear mixer operating at 24 rpm for 10-30 minutes. The lubricant was then screened into the mixer and the materials were blended for a further 2-5 minutes. The resulting lubricated mixture was compressed into 350 mg pillow-shaped tablets using a Kilian S100 tableting machine.

Example 2

Coated sustained-release tablets of pramipexole dihydrochloride were prepared having the composition shown in Table 2.

TABLE 2

Composition of coated tablets of Example 2

| Ingredient | Amount (mg) |
|---|---|
| pramipexole dihydrochloride monohydrate | 0.375 |
| HPMC type 2208, 4000 mPa s | 140.0 |
| pregelatinized starch | 206.5 |
| colloidal silicon dioxide | 1.4 |
| magnesium stearate | 1.75 |
| total core | 350 |
| ethylcellulose-based coating material (Surelease ®) | 7.88 |
| HPMC-based coating material (Opadry ®) | 2.63 |
| total coating | 10.5 |

Tablet cores were prepared exactly as in Example 1. A coating solution was prepared as follows. Opadry® HPMC-based material in an amount of 6.004 g was added to 106.682 g water and mixed for 45 minutes to provide an HPMC mixture. Next, 72.045 g Surelease® ethylcellulose-based material was added to the HPMC mixture and mixed for an additional 30 minutes to provide a coating solution.

The coating solution was applied to the tablet cores in an amount providing a 3% weight gain. The resulting coated tablets were cured using a 12 inch (about 30 cm) Vector LCDS or 24 inch (about 60 cm) Thomas Accela-Coata coating pan for about 15 minutes at a bed temperature of at least about 70° C. After curing, temperature was ramped down over a period of about 8 minutes to an exhaust temperature of about 45° C.

Example 3

Coated sustained-release tablets of pramipexole dihydrochloride were prepared having the composition shown in Table 3.

TABLE 3

Composition of coated tablets of Example 3

| Ingredient | Amount (mg) |
|---|---|
| pramipexole dihydrochloride monohydrate | 0.375 |
| HPMC type 2208, 4000 mPa s | 140.0 |
| pregelatinized starch | 206.5 |
| colloidal silicon dioxide | 1.4 |
| magnesium stearate | 1.75 |
| total core | 350 |
| ethylcellulose-based coating material (Surelease ®) | 8.4 |
| HPMC-based coating material (Opadry ®) | 2.1 |
| total coating | 10.5 |

Tablet cores were prepared exactly as in Example 1. A coating solution was prepared as follows. Opadry® HPMC-based material in an amount of 4.801 g was added to 103.041 g water and mixed for 45 minutes to provide an HPMC mixture. Next, 76.819 g Surelease® ethylcellulose-based material was added to the HPMC mixture and mixed for an additional 30 minutes to provide a coating solution.

Coating to a 3% weight gain and curing of the coated tablets were performed exactly as in Example 2.

Example 4

Coat sustained-release tablets of pramipexole dihydrochloride were prepared having the composition shown in Table 4.

TABLE 4

Composition of coated tablets of Example 4

| Ingredient | Amount (mg) |
|---|---|
| pramipexole dihydrochloride monohydrate | 0.375 |
| HPMC type 2208, 4000 mPa s | 140.0 |
| pregelatinized starch | 206.5 |
| colloidal silicon dioxide | 1.4 |
| magnesium stearate | 1.75 |
| total core | 350 |
| ethylcellulose-based coating material (Surelease ®) | 13.13 |
| HPMC-based coating material (Opadry ®) | 4.38 |
| total coating | 17.5 |

Tablet cores were prepared exactly as in Example 1. A coating solution was prepared as follows. Opadry® HPMC-based material in an amount of 10.003 g was added to 177.737 g water and mixed for 45 minutes to provide an HPMC mixture. Next, 120.03 g Surelease® ethylcellulose-based material was added to the HPMC mixture and mixed for an additional 30 minutes to provide a coating solution.

Coating to a 3% weight gain and curing of the coated tablets were performed exactly as in Example 2. After this first curing step, coating was repeated to provide a total tablet weight gain of about 5%, followed by curing for about 15 minutes at a bed temperature of at least about 70° C. After curing, temperature was ramped down over a period of about 8 minutes to an exhaust temperature of about 45° C.

Example 5

Coated sustained-release tablets of pramipexole dihydrochloride were prepared having the composition shown in Table 5.

TABLE 5

Composition of coated tablets of Example 5

| Ingredient | Amount (mg) |
|---|---|
| pramipexole dihydrochloride monohydrate | 0.375 |
| HPMC type 2208, 4000 mPa s | 140.0 |
| pregelatinized starch | 206.5 |
| colloidal silicon dioxide | 1.4 |
| magnesium stearate | 1.75 |
| total core | 350 |
| ethylcellulose-based coating material (Surelease ®) | 14.0 |
| HPMC-based coating material (Opadry ®) | 3.5 |
| total coating | 17.5 |

Tablet cores were prepared exactly as in Example 1. A coating solution was prepared as follows. Opadry® HPMC-based material in an amount of 8.002 g was added to 171.735 g water and mixed for 45 minutes to provide an HPMC mixture. Next, 128.032 g Surelease® ethylcellulose-based material was added to the HPMC mixture and mixed for an additional 30 minutes to provide a coating solution.

Coating to a 5% total weight gain and curing of the coated tablets were performed exactly as in Example 2.

Example 6

Dissolution profiles of the pramipexole dihydrochloride tablets of each of Examples 1, 2 and 5 were evaluated in a standard in vitro USP dissolution assay under the following conditions. USP apparatus 1 was used to stir a dissolution medium (900 ml of 0.05M phosphate buffer at a pH of 6.8) at a spindle rotation speed of 100 rpm and a temperature of 37° C.

Figure 1:
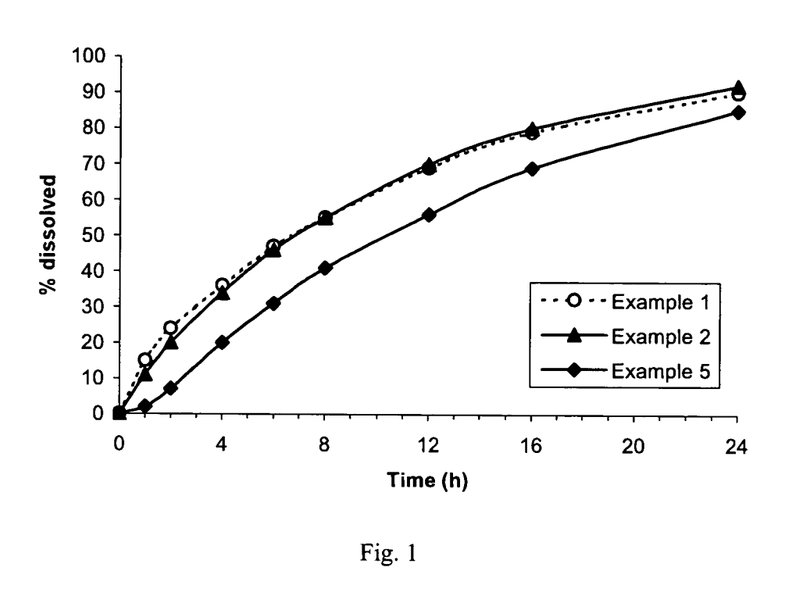
FIG. 1 is a graph showing in vitro dissolution profiles of three different 0.375 mg sustained-release tablet formulations of pramipexole dihydrochloride monohydrate, as more fully described in Example 6.

Data are shown in FIG. 1. The uncoated tablet of Example 1 and the tablet of Example 2 having a 3% coating comprising 25% pore-former exhibited very similar overall dissolution profiles. On close inspection, however, it will be noticed that the uncoated tablet of Example 1 showed faster initial dissolution, such that at 1 hour and 2 hour sampling times the percent dissolved was greater, than in the case of the coated tablet of Example 2. For example, at 1 hour, the coated tablet of Example 2 showed only 11% dissolution, while the uncoated tablet of Example 1 showed 15% dissolution. Similarly, at 2 hours, the coated tablet of Example 2 showed no more than 20% dissolution, while the uncoated tablet of Example 1 showed 24% dissolution.

Dissolution of the tablet of Example 5 having a 5% coating comprising 20% pore-former exhibited a dissolution profile much slower than either the tablet of Example 1 or the tablet of Example 2.

Example 7

An in vivo study was conducted in healthy human volunteers to assess bioavailability of pramipexole formulated as the sustained-release or extended-release (XR) tablets of Examples 1, 2 and 5 by comparison with a reference treatment with immediate-release (IR) pramipexole dihydrochloride tablets, and to evaluate safety of pramipexole when its absorption profile is altered as in these extended-release tablets.

Method

The study followed an open-label, 4-way, randomized crossover design and was conducted in healthy male and female subjects ranging from 18 to 55 years of age. The subjects received each of the four treatments during the course of the study, which was conducted at a single center. A total of 12 subjects were enrolled. The subjects were fasted overnight and then given a 0.375 mg oral dose of pramipexole dihydrochloride monohydrate. In the case of the IR formulation, which was provided as Mirapex® tablets, three equally divided doses of 0.125 mg each were given at 8-hour intervals, beginning in the morning. In the case of the XR formulations of Examples 1, 2 and 5, a single 0.375 mg tablet was given in the morning. Serial blood samples were taken over a 48-hour period for PK assessment. Adverse events were recorded during the same 48-hour period.

Plasma pramipexole concentrations were quantitated by an HPLC-MS/MS method, validated over the assay range 0.05-15 ng/ml. All runs met bioanalytical acceptance criteria for calibration standards and quality control. Samples were not diluted prior to analysis as all sample concentrations were within the limits of quantitation.

PK parameters for pramipexole were estimated by non-compartmental methods, using the nonlinear regression program Kinetica of Innaphase. Individual plasma concentration data and the actual time-points of blood sampling from each subject were used in the analysis. Plasma concentrations below the lower limit of quantitation at early time-points were set to zero, whereas those in the terminal phase were excluded from the analysis.

In vivo pramipexole absorption data were derived by a deconvolution routine employing the Kinetica program. To perform this analysis, a fit of the pramipexole data from the reference treatment was first made to a one-compartment open PK disposition model with first order absorption. Based on this fit, plasma pramipexole concentrations were simulated for a 0.375 mg intravenous bolus dose of pramipexole. These simulated pramipexole concentrations were used in the deconvolution routine.

In vitro/in vivo correlations for each of the pramipexole XR formulations were examined by evaluating a linear relationship of in vivo absorption as a function of in vitro dissolution.

Prediction of mean steady-state concentrations arising from repeated daily dosing was performed by interpolation of hourly concentrations from individual subjects' observed concentration/time data and then by the principle of superposition, estimating the concentrations during the 6th day of dosing. Estimates of half-life obtained from this study, which were consistent with values reported previously, indicate that steady state would be achieved by the 4th day. The steady-state parameters $T_{max}$, $C_{max}$, $C_{min}$, $AUC_{0-\tau}$, $C_{avg}$ (calculated as $AUC_{0-24}/\tau$) and FR (fluctuation ratio, calculated as $(C_{max}-C_{min})/C_{avg}$) were also estimated during this exercise.

Results

Of the 12 subjects enrolled, 10 completed the study. Two subjects were dropped prior to receiving the reference treatment, therefore their data were not included in the PK analysis.

Figure 2:
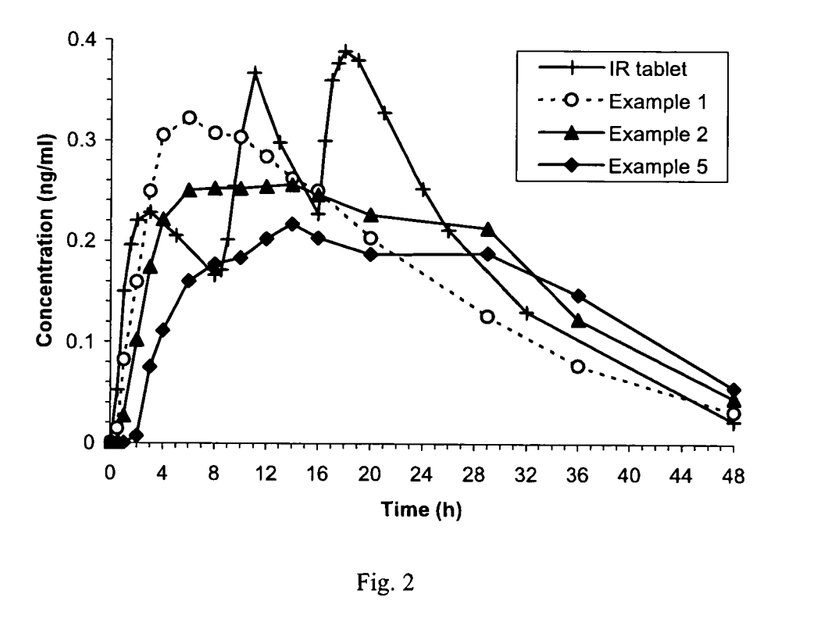
FIG. 2 is a graph from a human PK study showing time course of mean plasma pramipexole concentration following oral administration of 0.375 mg pramipexole dihydrochloride monohydrate, either as a 0.125 mg immediate-release tablets administered three times at 8-hour intervals or as a single 0.375 mg dose of each of three different sustained-release tablets, as more fully described in Example 7.

Mean plasma pramipexole concentrations over the 48-hour assessment period are shown in FIG. 2. PK estimates derived from the individual subject data are provided in Table 6.

TABLE 6

PK parameters (mean ± standard deviation)

| Parameter | IR tablet (Mirapex ®) | XR tablets | | |
|---|---|---|---|---|
| | | Example 1 | Example 2 | Example 5 |
| $AUC_{0-\infty}$ (ng · h/ml) | 9.93 ± 3.05 | 9.05 ± 3.24 | 9.66 ± 2.91 | 8.91 ± 4.15 |
| $AUC_{0-48}$ (ng · h/ml) | 8.60 ± 2.63 | 7.76 ± 2.83 | 7.60 ± 2.00 | 7.07 ± 2.77 |
| $C_{max}$ (ng/ml) | 0.433 ± 0.083* | 0.332 ± 0.076 | 0.282 ± 0.069 | 0.242 ± 0.062 |
| $T_{max}$ (h) | 15.9 ± 3.4* | 6.2 ± 2.0 | 12.0 ± 5.3 | 15.6 ± 6.2 |
| $T_{1/2}$ (h) | 9.1 ± 2.6 | 11.4 ± 4.1 | 11.9 ± 2.8 | 12.1 ± 6.0 |

*reached after third 0.125 mg tablet

Mean cumulative absorption data (up to 24 hours) for the XR tablets are shown in Table 7, together with corresponding in vitro dissolution data from Example 6.

TABLE 7

In vitro dissolution and in vivo absorption data for XR tablets

| | Example 1 | | Example 2 | | Example 5 | |
|---|---|---|---|---|---|---|
| Time (h) | % diss. (in vitro) | % abs. (in vivo) | % diss. (in vitro) | % abs. (in vivo) | % diss. (in vitro) | % abs. (in vivo) |
| 0 | 0 | 0.0 | 0 | 0.0 | 0 | 0.0 |
| 1 | 15 | 10.6 | 11 | 3.3 | 2 | 0.0 |
| 2 | 24 | 21.1 | 20 | 13.2 | 7 | 0.5 |
| 4 | 36 | 43.2 | 34 | 30.0 | 20 | 15.0 |
| 6 | 47 | 52.3 | 46 | 39.4 | 31 | 23.9 |
| 8 | 55 | 57.8 | 55 | 45.6 | 41 | 29.6 |
| 12 | 69 | 68.6 | 70 | 57.1 | 56 | 41.6 |
| 16 | 79 | 75.5 | 80 | 67.4 | 69 | 51.1 |
| 24 | 90 | 83.6 | 92 | 83.2 | 85 | 64.8 |

Figure 4:
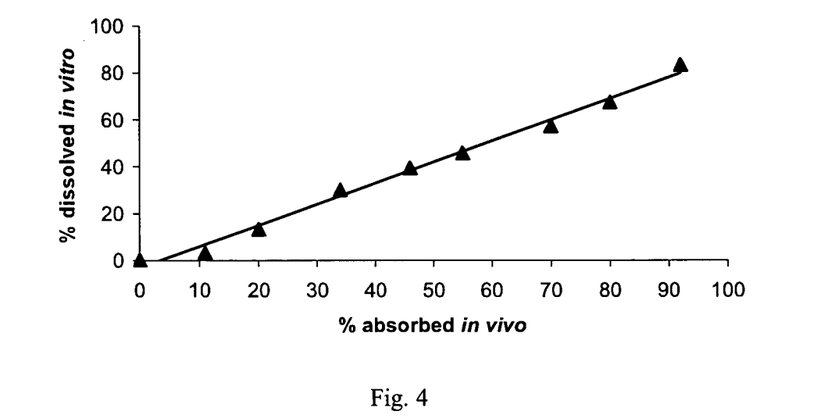
FIG. 4 shows in vitro/in vivo correlation for the pramipexole dihydrochloride tablets of Example 2.
Figure 5:
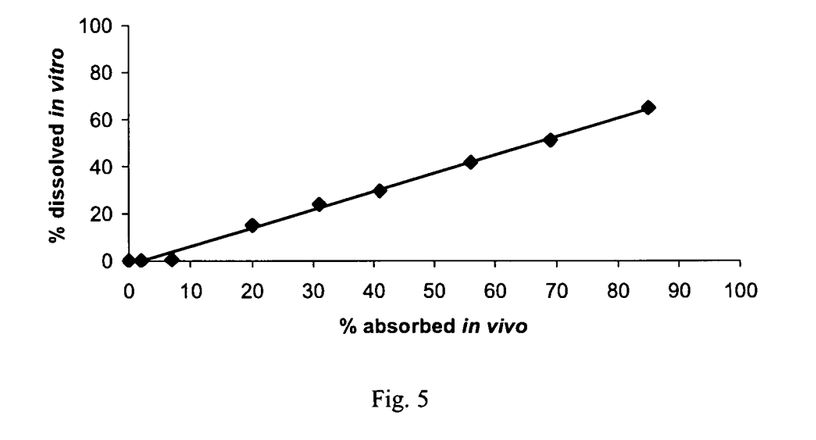
FIG. 5 shows in vitro/in vivo correlation for the pramipexole dihydrochloride tablets of Example 5.

In vitro/in vivo correlation plots derived from the data of Table 7 are shown in FIGS. 3-5 for the XR tablets of Examples 1, 2 and 5 respectively.

Estimated PK parameters calculated from predicted steady-state concentrations are given in Table 8.

TABLE 8

Estimated steady-state PK parameters (mean ± standard deviation)

| Parameter | IR tablet (Mirapex ®) | XR tablets | | |
|---|---|---|---|---|
| | | Example 1 | Example 2 | Example 5 |
| $T_{max}$ (h) | | 5.4 ± 1.9 | 5.6 ± 1.3 | 8.0 ± 2.8 |
| $C_{max}$ (ng/ml) | 0.53 ± 0.13 | 0.49 ± 0.15 | 0.48 ± 0.14 | 0.41 ± 0.14 |
| $C_{min}$ (ng/ml) | 0.29 ± 0.14 | 0.22 ± 0.12 | 0.27 ± 0.11 | 0.25 ± 0.15 |
| $C_{avg}$ (ng/ml) | 0.40 ± 0.13 | 0.36 ± 0.14 | 0.38 ± 0.12 | 0.34 ± 0.15 |
| $AUC_{0-\tau}$ (ng · h/ml) | 9.63 ± 3.12 | 8.66 ± 3.29 | 9.00 ± 2.92 | 8.06 ± 3.52 |
| FR | 066 ± 0.22 | 0.87 ± 0.31 | 0.61 ± 0.18 | 0.62 ± 0.45 |

The subjects dropped from the study experienced a non-serious adverse event, orthostatic hypotension. Both subjects were receiving treatment with the XR tablet of Example 1 when this adverse event occurred.

No serious adverse events were reported in the study. The most frequently reported event was orthostatic hypotension, all but two of which were considered transient in nature. The numbers of individual non-serious adverse events reported for each treatment are given in Table 9.

TABLE 9

Numbers of non-serious adverse events reported

| | IR tablet (Mirapex ®) | XR tablets | | |
|---|---|---|---|---|
| | | Example 1 | Example 2 | Example 5 |
| No. of subjects | 10 | 12 | 11 | 10 |
| All events | 9 | 17 | 8 | 5 |
| Orthostatic hypotension | 1 | 5 | 2 | 1 |

Discussion

The mean plasma pramipexole concentration profile shown in FIG. 2 clearly shows the tablets of Examples 1, 2 and 5 effectively extended the release of pramipexole relative to the IR tablet. The XR tablets of Examples 1 and 2 exhibit a delay of approximately 1 hour in onset of absorption, whereas quantifiable levels of pramipexole were not observed until about 3 hours after administration of the XR tablet of Example 5.

The derived PK parameters given in Table 6, in particular the $C_{max}$ and $T_{max}$ data, indicate that of the XR tablets, the tablet of Example 1 exhibited the fastest and the tablet of Example 5 the slowest absorption, the tablet of Example 2 being intermediate in this regard.

The relatively high incidence of non-serious adverse events associated with the tablet of Example 1 suggests that the relatively rapid release of pramipexole from this formulation, leading to a relatively high $C_{max}$, is detrimental to the safety profile of such a formulation. On the other hand, the tablets of Examples 2 and 5 exhibit a safety profile that is at least as favorable as the IR tablet administered three times daily. As shown in Table 8, the predicted fluctuation ratio was also greatest for the tablet of Example 1.

As shown in FIGS. 3-5, a strong in vitro/in vivo correlation was established within each formulation. Surprisingly, however, the in vitro dissolution data did not clearly distinguish the uncoated tablet of Example 1 from the coated tablet of Example 2, except, as pointed out above, at the earliest sampling times.

What is claimed is:

1. An orally deliverable pharmaceutical once daily sustained release composition comprising about 0.1 to about 10 mg of pramipexole dihydrochloride monohydrate a starch in an amount of about 25% to about 75% by weight, a hydrophilic polymer in an amount of about 20% to about 70% by weight, wherein said pramipexole is dispersed in hydrophilic polymer and starch, and said hydrophilic polymer functions to provide sustained release of said pramipexole, said composition exhibiting at least one of (a) an in vitro release profile wherein on average no more than about 20% of the pramipexole is dissolved within 2 hours after placement of the composition in a standard dissolution test conducted according to USP24 using Apparatus 1 with a spindle rotation speed of 100 rpm and a dissolution medium of 0.05M phosphate buffer, pH 6.8, at 37° C.; and (b) an in vivo pramipexole absorption profile following single dose oral administration to healthy adult humans wherein the time to reach a mean of 20% absorption is greater than about 2 hours and/or the time to reach a mean of 40% absorption is greater than about 4 hours wherein said composition comprises a full daily dose contained in a single dose unit, further wherein said composition, when administered once daily, exhibits a bioavailability substantially equivalent to an equal daily dose of an immediate-release pramipexole dihydrochloride reference formulation administered three times a day.

2. The composition of claim 1 wherein no more than about 12% of the pramipexole dihydrochloride monohydrate dissolves within 1 hour in said test.

3. The composition of claim 1 wherein time to reach 50% dissolution is at least about 4 hours.

4. The composition of claim 1 wherein time to reach 50% dissolution is at least about 6 hours.

5. The composition of claim 1 wherein time to reach 50% dissolution is at least about 8 hours.

6. The composition of claim 1 wherein time to reach 50% dissolution is at least about 12 hours.

7. The composition of claim 1 that exhibits an in vivo pramipexole absorption profile following single dose oral administration to healthy adult humans wherein the time to reach a mean of 20% absorption is greater than about 2 hours and/or the time to reach a mean of 40% absorption is greater than about 4 hours.

8. The composition of claim 7 wherein the time to reach a mean of 40% absorption is at least about 5 hours.

9. The composition of claim 7 wherein the time to reach a mean of 40% absorption is at least about 6 hours.

10. The composition of claim 1 that, following single dose administration of 0.375 mg, expressed as pramipexole dihydrochloride monohydrate equivalent, exhibits a maximum plasma concentration ($C_{max}$) of pramipexole that is not greater than about 0.3 ng/ml.

11. The composition of claim 1 that exhibits a time to reach maximum plasma concentration ($T_{max}$) of pramipexole that is at least about 6 hours following administration of the composition.

12. The composition of claim 1 that exhibits a time to reach maximum plasma concentration ($T_{max}$) of pramipexole that is at least about 8 hours following administration of the composition.

13. The composition of claim 1 that exhibits a pharmacokinetic profile consistent with steady-state plasma concentrations having a fluctuation ratio that is not substantially greater than that of an equal daily dose of an immediate-release pramipexole dihydrochloride reference formulation, administered three times a day.

14. The composition of claim 1 that is in the form of discrete dosage units.

15. The composition of claim 14 that comprises about 0.2 to about 6 mg pramipexole, expressed as pramipexole dihydrochloride monohydrate equivalent, per dosage unit.

16. The composition of claim 14 that comprises about 0.3 to about 5 mg pramipexole, expressed as pramipexole dihydrochloride monohydrate equivalent, per dosage unit.

17. The composition according to claim 1, wherein the amount of pramipexole dihydrochloride monohydrate is 0.375 mg.

18. The composition according to claim 1, wherein the amount of pramipexole dihydrochloride monohydrate is 0.5 mg.

19. The composition according to claim 1, wherein the amount of pramipexole dihydrochloride monohydrate is 0.75 mg.

20. The composition according to claim 1, wherein the amount of pramipexole dihydrochloride monohydrate is 1.0 mg.

21. The composition according to claim 1, wherein the amount of pramipexole dihydrochloride monohydrate is 1.5 mg.

22. The composition according to claim 1, wherein the amount of pramipexole dihydrochloride monohydrate is 3.0 mg.

23. The composition according to claim 1, wherein the amount of pramipexole dihydrochloride monohydrate is 4.5 mg.

24. The composition according to claim 1, wherein the amount of starch is about 40% to about 70% by weight.

25. The composition according to claim 1, wherein the amount of starch is about 45% to about 65% by weight.

26. The composition according to claim 1, wherein the amount of the hydrophilic polymer is about 30% to about 60% by weight.

27. The composition according to claim 1, wherein the amount of the hydrophilic polymer is about 35% to about 60% by weight.

28. The composition according to claim 1, wherein the amount of the hydrophilic polymer is about 35% to about 50% by weight.

29. The composition according to claim 1 in the form of a tablet.

30. The composition of claim 1 that exhibits an in vitro release profile wherein on average no more than about 20% of the pramipexole is dissolved within 2 hours after placement of the composition in a standard dissolution test conducted according to USP24 using Apparatus 1 with a spindle rotation speed of 100 rpm and a dissolution medium of 0.05M phosphate buffer, pH 6.8, at 37° C.

31. A method of treatment of a subject having Parkinson's disease, the method comprising orally administering to the subject, not more than once daily, the composition of claim 1.

* * * * *